United States Patent [19]
Gagne

[11] Patent Number: 5,311,882
[45] Date of Patent: May 17, 1994

[54] TOMOGRAPHY HEAD RESTRAINT

[76] Inventor: George J. Gagne, R.F.D. 1, Box 261, Epsom, N.H. 03234

[21] Appl. No.: 87,382

[22] Filed: Jul. 8, 1993

[51] Int. Cl.⁵ .......................... A61G 15/00; A61F 5/37
[52] U.S. Cl. .................................. 128/845; 128/870; 128/DIG. 20
[58] Field of Search ............... 128/869, 870, DIG. 20, 128/845; 602/13, 16, 17; 5/630, 631, 634, 636, 637, 638

[56] References Cited

U.S. PATENT DOCUMENTS

| | | |
|---|---|---|
| 1,884,927 | 10/1932 | Van Raalte . |
| 2,589,155 | 3/1952 | Smith . |
| 3,312,213 | 4/1967 | Timm .......................... 602/13 |
| 3,397,688 | 8/1968 | Gottfried ..................... 602/13 |
| 3,982,132 | 9/1976 | Kay ......................... 128/DIG. 20 |
| 4,034,748 | 7/1977 | Winner ....................... 128/870 |
| 4,182,322 | 1/1980 | Miller . |
| 4,301,791 | 11/1981 | Franco ........................ 128/870 |
| 4,385,627 | 5/1983 | Nelson ........................ 602/17 |
| 4,400,820 | 8/1983 | O'Dell et al. . |
| 4,576,150 | 3/1986 | Aurscher . |
| 4,682,587 | 7/1987 | Curlee . |
| 4,805,603 | 2/1989 | Cumberland ............... 128/DIG. 20 |
| 5,076,264 | 12/1991 | Lonardo . |
| 5,133,776 | 7/1992 | Crowder ..................... 128/DIG. 20 |
| 5,137,024 | 8/1992 | Souma . |
| 5,207,716 | 5/1993 | McReynolds ............... 128/870 |

Primary Examiner—Michael A. Brown
Attorney, Agent, or Firm—Richard C. Litman

[57] ABSTRACT

A head restraint for immobilizing a patient during tomographic examination. A two part cover, each part enclosing a pneumatic, inflatable member, is adjustably assembled so as to locate each inflatable member on opposite sides of the patient's head. A strap encircles the forehead, maintaining the restraint on the patient. A hand held squeeze bulb simultaneously and equally pressurizes both inflatable members so as to occupy all space between the patient's head and a U-shaped head holder typically provided with tomography X-ray machines. The inflatable members establish a comfortably fitting, flexible, large patch of contact with the patient's head and with the head holder. These characteristics immobilize a patient's head sufficiently to enable clear images to be developed. The inflated members are depressurized by a manual valve, and the restraint is readily removed from the patient.

12 Claims, 2 Drawing Sheets

TOMOGRAPHY HEAD RESTRAINT

BACKGROUND OF THE INVENTION

1. FIELD OF THE INVENTION

The present invention relates to a head restraint for immobilizing a supine patient's head during X-ray examination.

2. DESCRIPTION OF THE PRIOR ART

Immobilizing supports for the head of a medical patient have been the subject of prior patents. U.S. Pat. No. 4,400,820, issued on Aug. 23, 1983 to William R. O'Dell et al., discloses an immobilizing head holder for use during tomography comprising a U-shaped receptacle, a foam liner, and plural straps surrounding the head when the holder is in use, among other components.

A similar device, albeit not for tomography, is seen in U.S. Pat. No. 4,182,322, issued to Larry C. Miller on Jan. 8, 1980. Other support or immobilizing devices having pads and straps include U.S. Pat. Nos. 4,576,150, and 5,076,264, issued respectively to Walter Aurscher on Mar. 18, 1986 and to John S. Lonardo et al. on Dec. 31, 1991.

Fluid inflation of medical supports is shown in U.S. Pat. Nos. 1,884,927, issued on Oct. 25, 1932 to Martin Van Raalte; 2,589,155, issued on Mar. 11, 1952 to Raymond D. Smith; 4,682,587, issued on July 28, 1987 to James D. Curlee; and 5,137,024, issued on Aug. 11, 1992 to Takashiro Souma. Smith '155 shows two inflatable members. Carlee '587 discloses a separate pressurizing squeeze bulb and overlapping hook and loop fastener.

None of the above patents, taken either singly or in combination, is seen to describe the instant invention as claimed.

SUMMARY OF THE INVENTION

Tomography X-ray machines are typically provided with a U-shaped head holder designed to accommodate all patients, but this holder does not immobilize the head. Therefore, additional means must be provided in those cases wherein a patient must be restrained from moving the head. Of course, this encompasses minor, involuntary, or casual motion, it being impossible to restrain a violent patient or one determined to move the head under all circumstances.

It has been discovered from experience that a user's head is sufficiently immobilized by taking up the space between the head and the holder with a resilient yet firm member. The present invention provides two inflatable members, each enclosed within a cloth cover and located on opposite sides of the head. The cloth cover is formed in two parts adjustably attaching to one another by a hook and loop fastener. A strap secures the invention to the patient's head for the purpose of maintaining proper orientation of the device on the head, and not to immobilize the head.

Inflated cushioning members work well because pressure is equalized at all points of contact between the inflated member and the patient's head, and the X-ray machine head holder. Also, a flexible, inflatable member enables a substantial area of contact to exist between, firstly, the inflatable member and the head, and, secondly, the inflatable member and the head holder. The large, evenly pressurized area of contact assures adequate head immobilization. Also, pressure is adjustable for comfort, so that discomfort, which would cause squirming or other undesirable bodily motion, is avoided.

Accordingly, it is a principal object of the invention to provide a head restraint which effectively engages a patient's head and cooperates with a U-shaped head holder.

It is another object of the invention to provide a head restraint which is adjustably inflatable.

It is a further object of the invention to provide a head restraint wherein inflatable members provide flexible, conforming surfaces conforming to and having substantial area of contact with a patient's head and with a head holder which is provided with an X-ray machine.

Still another object of the invention is to provide a head restraint which is manually and readily donned, doffed, inflated, and deflated.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
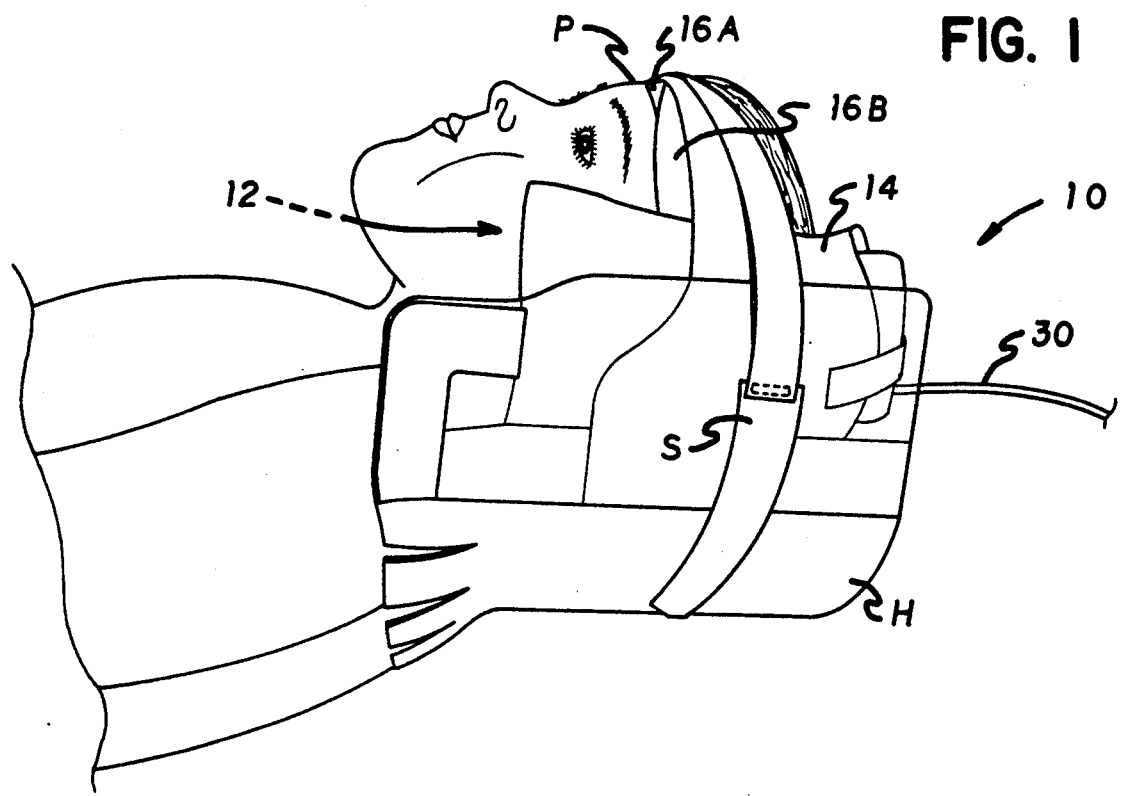
FIG. 1 is a partial side elevational view of the components of the invention, as worn by a supine patient.

The present invention is seen as deployed in FIG. 1. A patient P undergoing tomographic examination lies with his or her head held in a head holder H. The novel head restraint 10 is retained on the patient's head. Straps S provided with the X-ray machine hold the patient's head down, against head holder H, but do not prevent head movement. Head movement is opposed by inflatable members 12, 12 (see FIG. 3) held within a two part fabric cover 14. Cover 14 includes overlying straps 16A, 16B which enable cover 14 to partially encircle the head. This retains head restraint 10 on the patient, immobilization being provided by cooperation between inflated members 12, 12 and head holder H.

Figure 2:
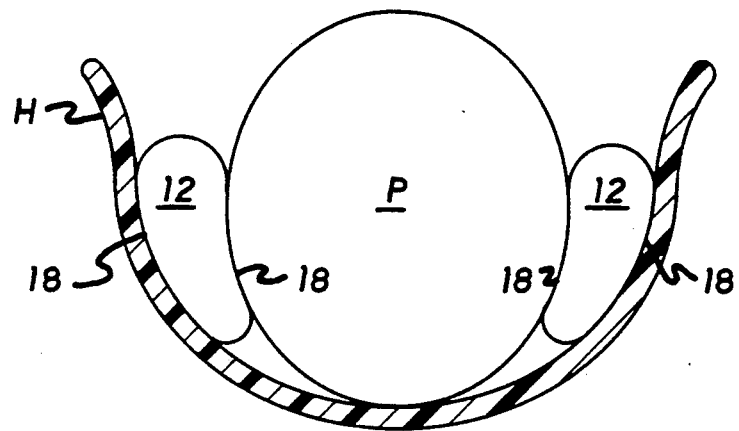
FIG. 2 is a largely diagrammatic view showing the relationship of the inflatable members to a patient's head and to a head holder, viewed from the top of the head of a supine patient.

This critical relationship is shown diagrammatically in FIG. 2. Inflated members 12, 12 fit between the sides of the patient's head and rigid inner surfaces of head holder H. Each inflated member 12 or 12 has two flexible surfaces 18, 18 which, when under inflation, contact and conform to, respectively, both the head and head holder abutting surfaces, thus establishing substantial areas of contact therebetween. When inflated, all of the space in the local area between respective areas of contact between a member 12 and head holder H, and between that member 12 and the side of the patient's head is occupied. This will be referred to as partially occupying the space between the head and the head holder.

The size of the area of contact helps assure opposition to head motions. Also, the degree of pneumatic pressure can be adjusted for comfort and for immobilizing force.

Cover 14 is preferably made from a fabric selected, in part, due to comfortable feel when held against the skin. The interplay of the feel of the fabric, evenness of pneumatic pressure exerted over the area of contact, and the size of the area of contact combine to produce a comfortable fit of head restraint 10 when deployed. This is important in removing a cause of squirming or similar reaction to mildly uncomfortable stimulus, as might be provided by other pressurizing and cushioning arrangements. For example, even a resilient foam liner exerts uneven pressure, and lacks the resilience of a pneumatic member to establish broad contact with the patient. This may result in a mildly tickling or disturbing fit, with the end result that the patient, especially a small child, will squirm in an effort to find a comfortable fit, and thus disturb the X-ray or other imaging process.

Figure 3:
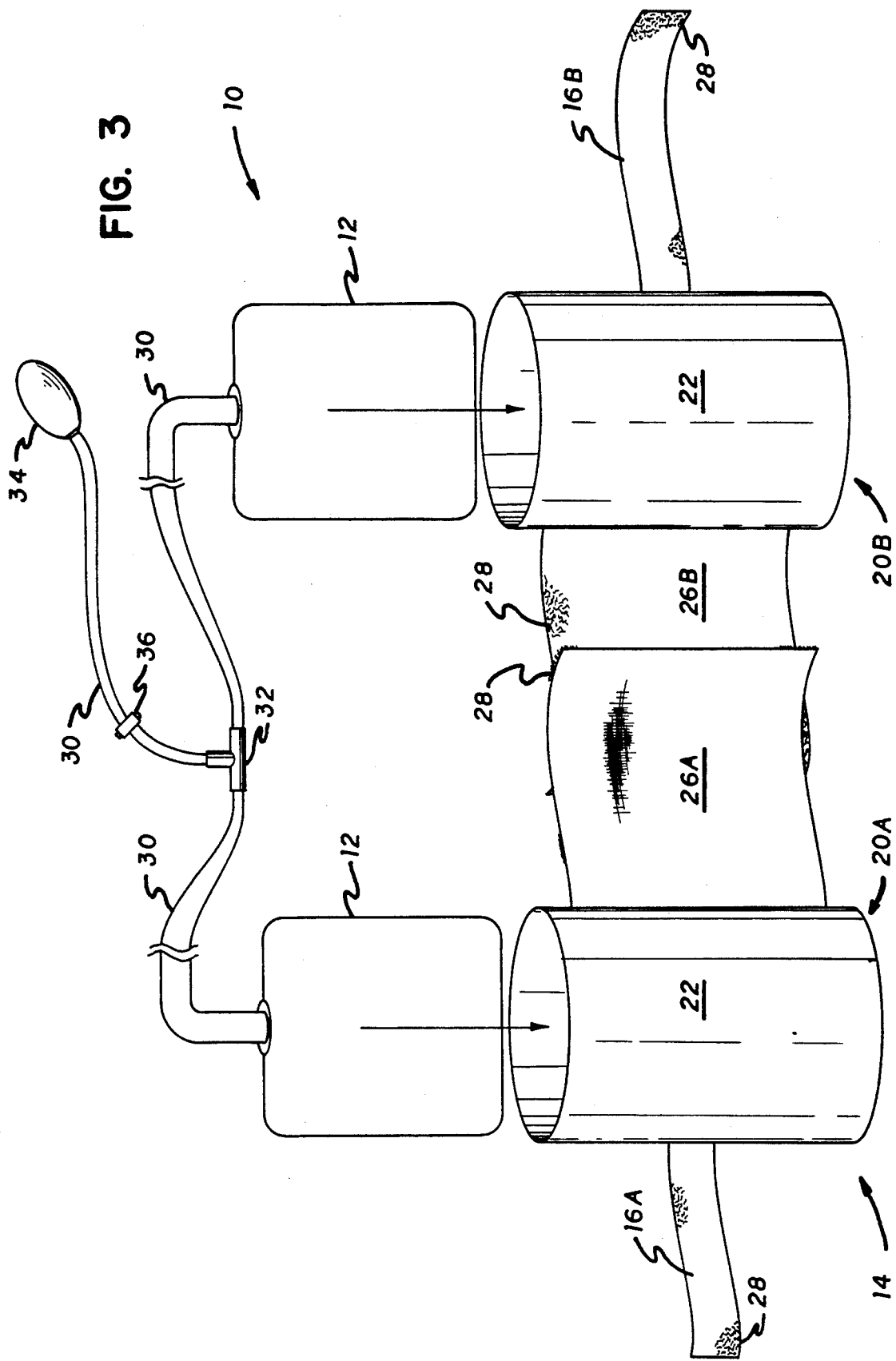
FIG. 3 is a perspective and somewhat diagrammatic view of the components of the invention.

Construction of head restraint 10 is seen in FIG. 3. Cover 14 comprises two, substantially mirror image parts 20A, 20B, each of which includes a pocket 22 for surroundably retaining one inflatable member 12. Cover parts 20A and 20B each have a strap 16A or 16B (respectively) for encircling the patient's head, and a tab 26A or 26B (respectively) cooperating with the other tab 26B or 26A. Tabs 26A,26B and straps 16A, 16B preferably have a corresponding hook and loop fastener 28 for ready attachment and separation. Tabs 26A,26B and straps 16A, 16B are selectively placed in overlying relationship so as to adjust the circumference of head restraint 10 while locating inflatable members 12, 12 advantageously for a particular patient.

Two inflatable members 12, 12 communicate by tubing 30 and a T-fitting 32 with a hand pump 34. Pump 34 includes a unidirectional inlet valve (not shown) maintaining pressure in the pneumatic system. A manual vent valve 36 releases pressure when deployment is no longer required. As seen in FIG. 1, tubing 30 extends away from the patient P, so that hand pump 34 is readily accessible, yet unobtrusive.

Head restraint 10 is quickly assembled and inflated for deployment, and quickly deflated and disassembled after use. The level of comfort experienced by the patient renders head restraint 10 highly effective. The uncomplicated construction enables construction at low cost, while maintaining effectiveness.

It is to be understood that the present invention is not limited to the sole embodiment described above, but encompasses any and all embodiments within the scope of the following claims.

I claim:

1. A head restraint comprising:
    a plurality of adjustably pressurized, inflatable members,
    fluid supply means enabling pressurization above ambient air pressure of said inflatable members,
    structural means for holding at least two of said inflatable members on opposite sides of a patient's head,
    said inflatable members being dimensioned and configured to enable said inflatable members to fit in and partially fill space between the patient's head and a head holder furnished with an X-ray machine,
    said structural means further comprising a structural flexible member having adjustment means for positioning and securing said head restraint in encirclement of the patient's head, and
    said structural flexible member further comprising a plurality of pockets collectively enclosing all of said inflatable members, whereby said inflatable members are inserted and withdrawn from said pockets when said head restraint is not deployed.

2. The head restraint according to claim 1, wherein said inflatable members each having two flexible surfaces which conform to an abutting, contacting surface when said inflatable members are inflated, said head restraint being configured such that, when deployed, for each one of said inflatable members, one of said two flexible surfaces contacts a side of a patient's head and the other of said two flexible surfaces contacts an inner surface of a head holder furnished with an X-ray machine, both of said flexible surfaces establishing a substantial area of contact with the patient's head and with the head holder.

3. The head restraint according to claim 1, wherein said structural flexible member further comprising at least two parts adjustably attachable to one another.

4. The head restraint according to claim 3,
    said structural flexible member further comprising
    at least one strap attachable to at least two of said at least two parts of said structural flexible member, said strap being arranged to partially encircle the patient's head, whereby said head restraint is retained on the patient's head when said inflatable members are not inflated.

5. The head restraint according to claim 4, wherein said at least two structural flexible member parts and said strap attach by hook and loop fastener.

6. The head restraint according to claim 1, wherein said fluid supply means comprising a hand pump, a manual, unidirectional inlet valve maintaining fluid pressure within said fluid supply means, and a manual vent valve selectively releasing fluid pressure from said fluid supply means.

7. The head restraint according to claim 6, wherein said fluid supply means communicating simultaneously with all of said inflatable members, whereby all of said inflatable members are evenly and simultaneously pressurized.

8. A head restraint comprising:
    a plurality of adjustably pressurized, inflatable members, each one of said inflatable members having two flexible surfaces which conform to an abutting, contacting surface when said inflatable members are inflated, said head restraint being configured such that, when deployed, for each one of said inflatable members, one of said two flexible surfaces contacts a side of a patient's head and the other of said two flexible surfaces contacts an inner surface of a head holder furnished with an X-ray machine, both of said flexible surfaces establishing a substantial area of contact with the patient's head and with the head holder,
    fluid supply means enabling pressurization above ambient air pressure of said inflatable members,
    structural means for holding at least two of said inflatable members on opposite sides of the patient's head, said head restraint being dimensioned and configured to enable said inflatable members to fit in and partially fill space between the patient's head and a head holder furnished with the X-ray machine,
    said structural means further comprising a flexible member having adjustment means for positioning and securing said head restraint in encirclement of the patient's head; and said structural flexible member further comprising a plurality of pocket members collectively enclosing all of said inflatable members, whereby said inflatable members are inserted and withdrawn from said pocket members when said head restraint is not deployed.

9. The head restraint according to claim 8, wherein said structural flexible member further comprising at least two parts adjustably attachable to one another.

10. The head restraint according to claim 9, said structural flexible member further comprising at least one strap attachable to at least two parts of said structural flexible member, said strap being arranged to partially encircle a patient's head, whereby said head restraint is retained on the patient's head when said inflatable members are not inflated.

11. The head restraint according to claim 10, wherein said at least two structural flexible member parts and said strap attached by hook and loop fastener.

12. A head restraint for immobilizing a supine patient's head for use with a tomography X-ray machine comprising:

a plurality of adjustably pressurized, inflatable members, each one of said inflatable members having two flexible surfaces which conform to an abutting, contacting surface when said inflatable members are inflated;

said head restraint being configured such that, when deployed, for each one of said inflatable members, one of said two flexible surfaces contacts a side of the patient's head and the other of said flexible surfaces contacts an inner surface of a head holder furnished with the X-ray machine, both of said flexible surfaces establishing a substantial area of contact with the patient's head and with the head holder;

fluid supply means enabling pressurization above air pressure of said inflatable members;

structural means for holding at least two of said inflatable members on opposite sides of the patient head, said head restraint being dimensioned and configured to enable said inflatable members to fit in and partially fill the space between the patient's head and a head holder furnished with then X-ray machine;

said structural means further comprising a structural flexible member having adjustment means for positioning and securing said head restraint in encirclement of the patient's head;

said structural flexible member further comprising a plurality of pockets collectively enclosing all of said inflatable members, whereby said inflatable members are inserted and withdrawn from said pockets when said head restraint is not deployed; and at least one strap attachable to at least two of said at least two parts of said structural flexible member, said strap being arranged to partially encircle the patient's head, whereby said head restraint is retained on the patient's head when said inflatable members are not inflated.

* * * * *